(12) United States Patent
Xiao et al.

(10) Patent No.: US 11,958,860 B2
(45) Date of Patent: Apr. 16, 2024

(54) CRYSTAL FORM OF COMPOUND, AND PREPARATION METHOD THEREFOR AND USE THEREOF

(71) Applicant: JIANGSU KANION PHARMACEUTICAL CO., LTD., Lianyungang (CN)

(72) Inventors: Wei Xiao, Lianyungang (CN); Wei Zhang, Lianyungang (CN); Yingguang Li, Lianyungang (CN); Qingming Guo, Lianyungang (CN); Shasha Gu, Lianyungang (CN); Hanfei Hu, Lianyungang (CN)

(73) Assignee: Jiangsu Kanion Pharmaceutical Co., Ltd., Lianyungang (CN)

( * ) Notice: Subject to any disclaimer, the term of this patent is extended or adjusted under 35 U.S.C. 154(b) by 0 days.

(21) Appl. No.: 18/273,083

(22) PCT Filed: Dec. 7, 2021

(86) PCT No.: PCT/CN2021/136107
§ 371 (c)(1),
(2) Date: Jul. 19, 2023

(87) PCT Pub. No.: WO2022/166369
PCT Pub. Date: Aug. 11, 2022

(65) Prior Publication Data
US 2024/0043437 A1 Feb. 8, 2024

(30) Foreign Application Priority Data
Feb. 2, 2021 (CN) .......................... 202110142974.3

(51) Int. Cl.
*C07D 491/147* (2006.01)

(52) U.S. Cl.
CPC ...... *C07D 491/147* (2013.01); *C07B 2200/13* (2013.01)

(58) Field of Classification Search
None
See application file for complete search history.

(56) References Cited

U.S. PATENT DOCUMENTS

2015/0099772 A1   4/2015  Grote

FOREIGN PATENT DOCUMENTS

CN        102796096 A        9/2016

OTHER PUBLICATIONS

Zhou et al. (Chem. Eur. J., 2016, 22, 7084). (Year: 2016).*
Supporting Information for Zhou et al. (Chem. Eur. J., 2016, 22, 7084). (Year: 2016).*

* cited by examiner

*Primary Examiner* — Sudhakar Katakam
*Assistant Examiner* — Jennifer C Sawyer
(74) *Attorney, Agent, or Firm* — Adam Bell; Matthew Kaser (57) ABSTRACT

The present invention discloses a crystal form A of a compound, where the compound is S-(−)-2,3-methylenedioxy-5,8,13,13a-tetrahydro-10,11-dimethoxy-6H-dibenzo[a,g]quinolizine, and an X-ray powder diffraction pattern of the crystal form A includes three or more 2θ values selected from the group consisting of: 12.21±0.2°, 13.381±0.2°, 15.181±0.2°, 16.171±0.2°, 17.101±0.2°, 19.801±0.2°, 21.511±0.2°, 24.391±0.2°, and 25.321±0.2°. The crystal form A of the compound of the present invention does not contain water and a solvent, has high stability and low hygroscopicity, and is suitable for patent medicine.

9 Claims, 7 Drawing Sheets

CRYSTAL FORM OF COMPOUND, AND PREPARATION METHOD THEREFOR AND USE THEREOF

BACKGROUND OF THE INVENTION

1. Technical Field

The present invention relates to the field of pharmaceutical chemistry, and in particular, to a crystal form of a compound and a preparation method therefor and a use thereof.

2. Description of Related Art

A S-(−)-2,3-methylenedioxy-5,8,13,13a-tetrahydro-10,11-dimethoxy-6H-dibenzo[a, g]quinolizine $\alpha_{1A}$-AR antagonist and a preparation method therefor are disclosed in WO2018041112A1.

Benign prostate hyperplasia is a common physiological disease in middle-aged and elderly men. More than half of men over 50 years old around the world suffer from prostate diseases, and such prostate diseases have become one of the main diseases in the urinary system of the elderly. At present, although some 5α-reductase inhibitors and α1 adrenergic receptor (α1-AR) antagonists have been used for treating benign prostate hyperplasia, these drugs still have several problems to be solved in terms of efficacy and safety, and side effects such as sexual dysfunction and postural hypotension have limited the efficacy thereof to a large extent. Therefore, it is of great significance to develop new, safe, and effective drugs to satisfy the demand of clinical medication for BPH patients.

Different crystal forms of drugs may affect their dissolution and absorption in vivo and then may affect their clinical efficacy and safety to some extent, and in particular, crystal forms of some insoluble oral solid or semi-solid preparations have a more serious impact on the above situations.

Therefore, it is necessary to develop a crystal form of a compound, where the crystal form has high stability, low hygroscopicity, and ease of processing.

BRIEF SUMMARY OF THE INVENTION

The objective of the present invention is to provide a crystal form of a compound of formula I, where the crystal form has high stability, low hygroscopicity, and ease of processing.

In view of this, the present invention proposes a crystal form A of a compound of formula I, an X-ray powder diffraction pattern of the crystal form A includes three or more 2θ values selected from the group consisting of:
12.21±0.2°, 13.381±0.2°, 15.181±0.2°, 16.171±0.2°, 17.101±0.2°, 19.801±0.2°, 21.511±0.2°, 24.391±0.2°, and 25.321±0.2°.

Further, the X-ray powder diffraction pattern of the crystal form A includes the 2θ value selected from the group consisting of:
12.21±0.2°, 13.381±0.2°, 15.181±0.2°, 16.171±0.2°, 17.101±0.2°, 19.801±0.2°, 21.511±0.2°, 24.391±0.2°, and 25.321±0.2°.

Further, the X-ray powder diffraction pattern of the crystal form A includes three or more 2θ values selected from the group consisting of:
12.21±0.1°, 13.381±0.1°, 15.181±0.1°, 16.171±0.1°, 17.101±0.1°, 19.801±0.1°, 21.511±0.1°, 24.391±0.1°, and 25.321±0.1°.

Further, a relative intensity corresponding to a position peak of the 2θ value is:

| Angle 2θ | Relative intensity |
| --- | --- |
| 12.21 ± 0.2° | 100 |
| 13.381 ± 0.2° | 2.5 ± 0.5 |
| 15.181 ± 0.2° | 4.48 ± 0.5 |
| 16.171 ± 0.2° | 7.05 ± 0.5 |
| 17.101 ± 0.2° | 17.79 ± 0.5 |
| 19.801 ± 0.2° | 14.02 ± 0.5 |
| 21.511 ± 0.2° | 6.47 ± 0.5 |
| 24.391 ± 0.2° | 6.56 ± 0.5 |
| 25.321 ± 0.2° | 5.44 ± 0.5 |

Further, the crystal form A has a characteristic peak at d values of three or more interplanar crystal spacings selected from the group consisting of: 7.2 Å±0.2 Å, 6.6 Å±0.2 Å, 5.8 Å±0.2 Å, 5.5 Å±0.2 Å, 5.2 Å±0.2 Å, 4.5 Å±0.2 Å, 4.1 Å±0.2 Å, 3.6 Å±0.2 Å, and 3.5 Å±0.2 Å.

Figure 2:
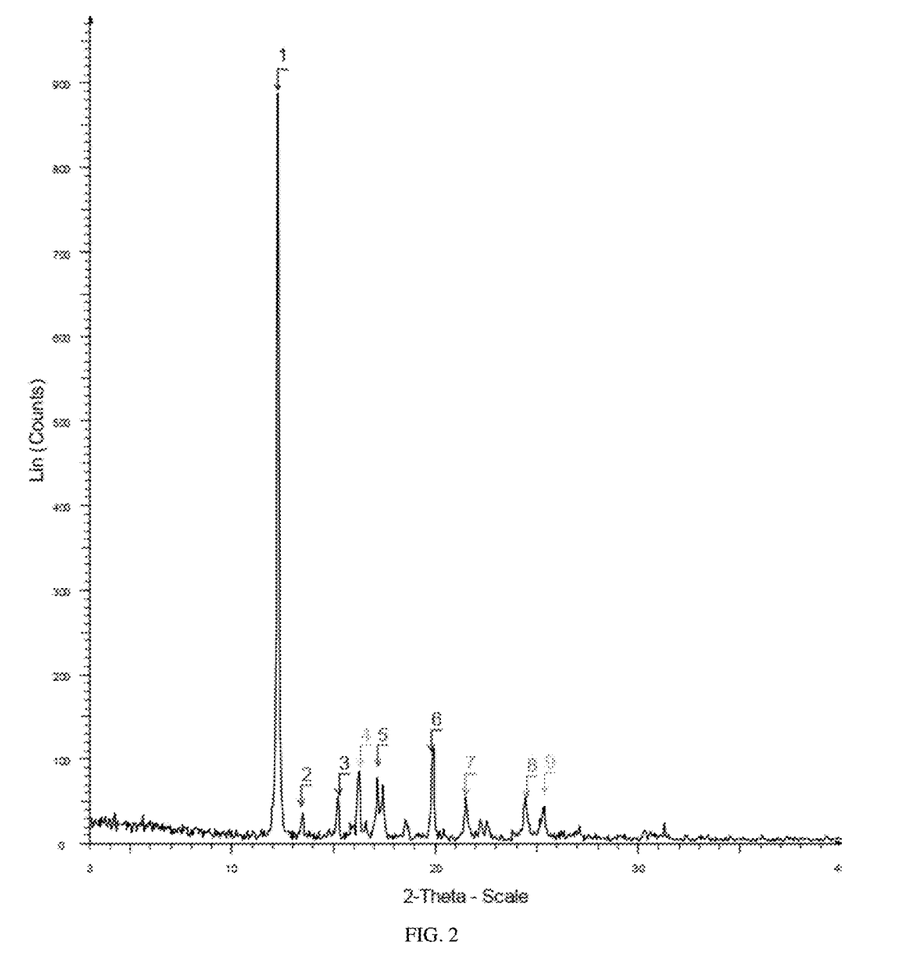
FIG. 2 shows an X-ray powder diffraction (XRPD) pattern of a crystal form A in Example 1.

Further, the crystal form A has the XRPD pattern substantially as shown in FIG. 2, or the X-ray powder diffraction pattern of the crystal form A is substantially as shown in Table 1; the 2θ value of each characteristic peak at the 2θ value optionally has an error margin of ±0.2°, or preferably has an error margin of ±0.1°.

Further, the crystal form A has one or more characteristics selected from the group consisting of:
1) a TGA pattern of the crystal form A having no gravimetric loss before the compound of formula I is decomposed;
2) a DSC pattern of the crystal form A having a characteristic absorption peak at a peak of 172±5° C. (or ±3° C., or ±1° C.); and 3) the crystal form A having a moisture-absorption weight gain of no more than 1% and preferably 0.4%±0.3% at a relative humidity of 0%-95%.

In another preferred embodiment, an IR spectrogram of the crystal form A includes three or more characteristic absorption peaks denoted as a wavelength of λ and selected from the group of consisting of: 3599±2 cm$^{-1}$, 3001±2 cm$^{-1}$, 2934±2 cm$^{-1}$, 2835±2 cm$^{-1}$, 2789±2 cm$^{-1}$, 1611±2 cm$^{-1}$, 1520±2 cm$^{-1}$, 1485±2 cm$^{-1}$, 1452±2 cm$^{-1}$, 1348±2 cm$^{-1}$, 1248±2 cm$^{-1}$, 1217±2 cm$^{-1}$, 1107±2 cm$^{-1}$, 1030±2 cm$^{-1}$, 995±2 cm$^{-1}$, 926±2 cm$^{-1}$, and 856±2 cm$^{-1}$; more preferably, each of the characteristic absorption peaks has an error margin of ±1 cm$^{-1}$.

Figure 3:
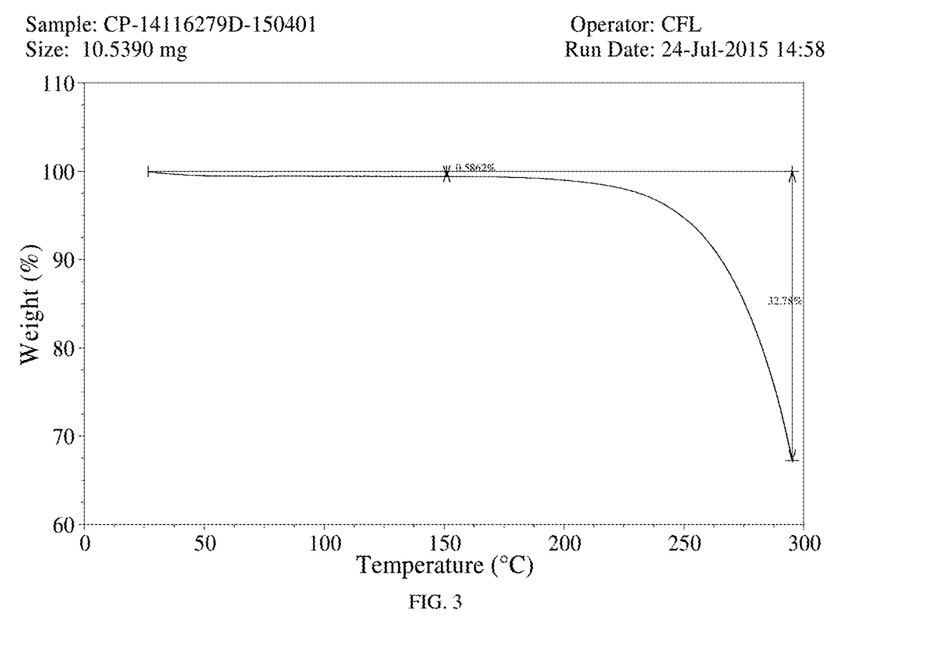
FIG. 3 shows a thermo gravimetric analysis (TGA) pattern of a crystal form A in Example 1.
Figure 4:
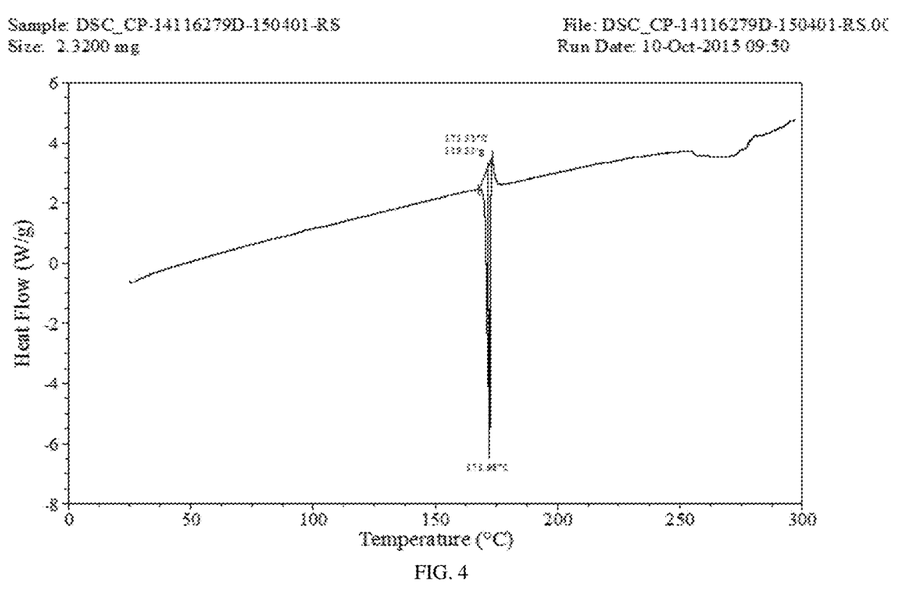
FIG. 4 shows a differential scanning calorimetry (DSC) pattern of a crystal form A in Example 1.
Figure 5:
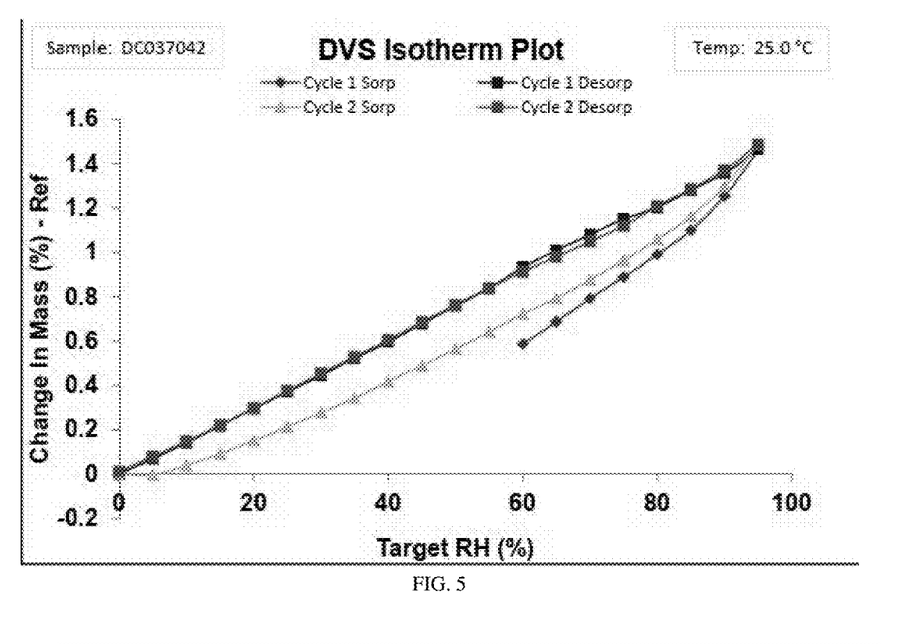
FIG. 5 shows a dynamic vapor sorption (DVS) pattern of a crystal form A in Example 1.
Figure 6:
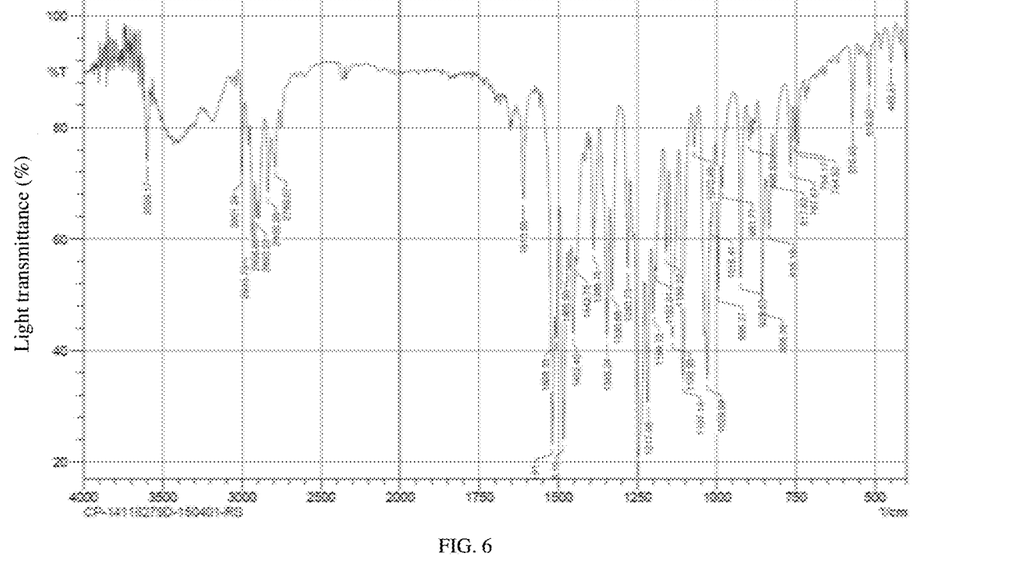
FIG. 6 shows an infrared (IR) spectrogram of a crystal form A in Example 1.
Figure 7:
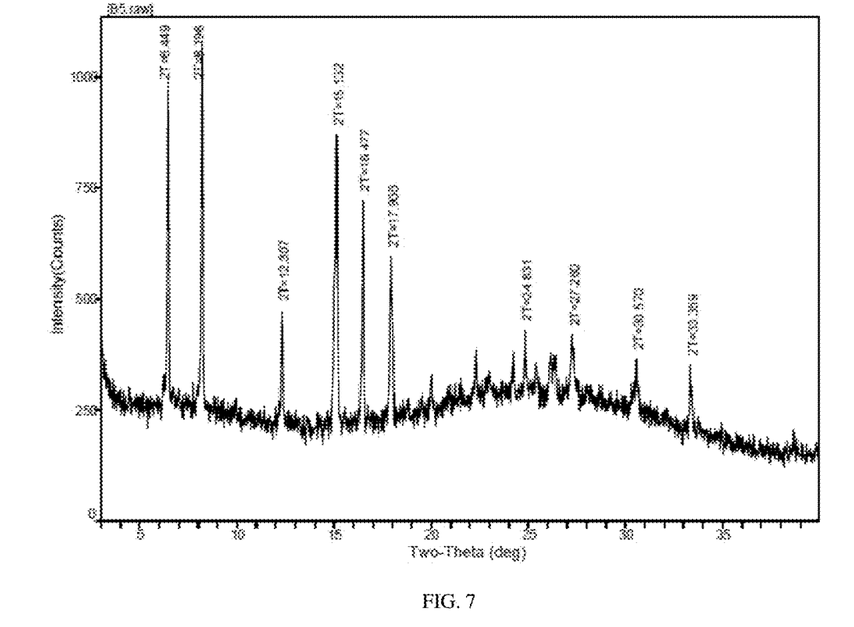
FIG. 7 shows an X-ray powder diffraction (XRPD) pattern of a crystal form B in Comparative Example 1.
Figure 8:
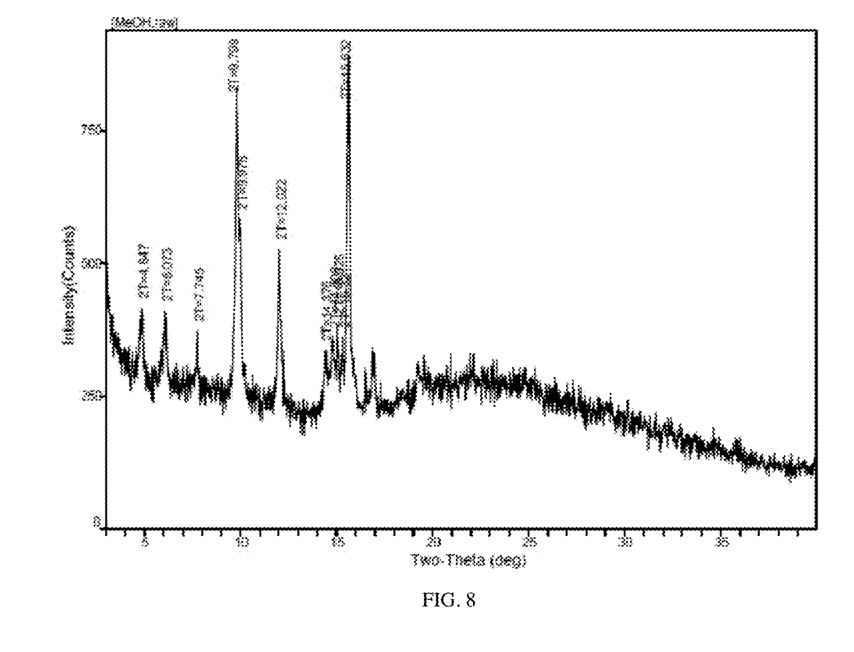
FIG. 8 shows an X-ray powder diffraction (XRPD) pattern of a crystal form C in Comparative Example 2.
Figure 9:
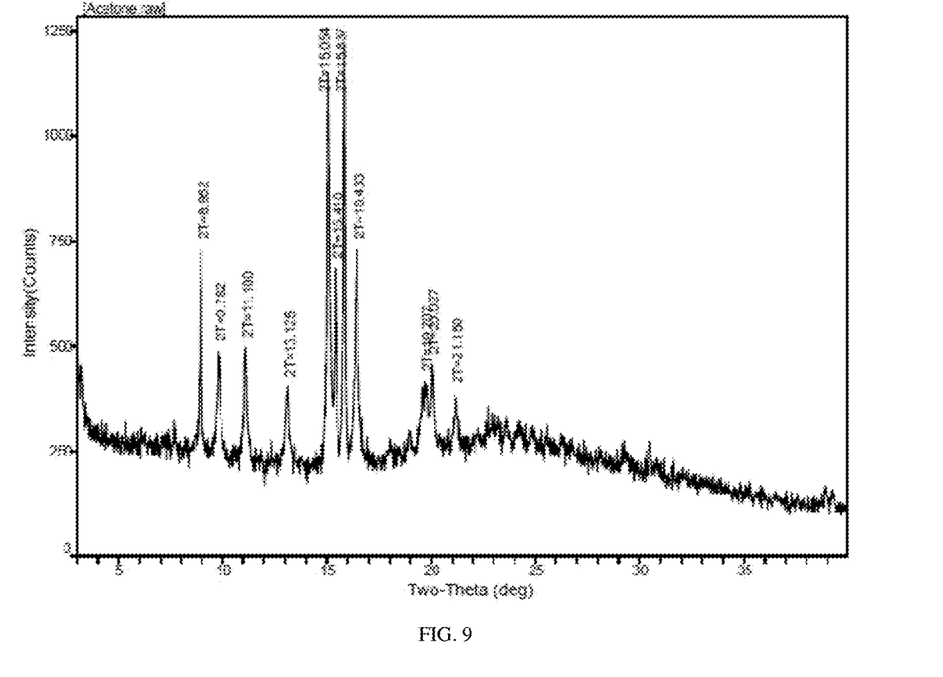
FIG. 9 shows an X-ray powder diffraction (XRPD) pattern of a crystal form D in Comparative Example 3.

Further, the crystal form A has one or more characteristics selected from the group consisting of:

1) the crystal form A having a TGA pattern substantially as shown in FIG. 3;
2) the crystal form A having a DSC pattern substantially as shown in FIG. 4;
3) the crystal form A having a DVS pattern substantially as shown in FIG. 5; and
4) the crystal form A having an IR spectrogram substantially as shown in FIG. 6.

The present invention further provides a crystalline composition, where the crystalline composition includes the crystal form A as described in any one of the foregoing.

In another preferred embodiment, based on a total weight of the crystalline composition, a weight percentage of the crystal form A is 60%-99.999%, preferably 80%-99.999%, and more preferably 90%-99.999%.

In another preferred embodiment, the crystalline composition further includes: a crystal of a compound of an amorphous form A in formula I or an amorphous compound of formula I.

The present invention further provides a preparation method for the crystal form A, and the method includes the following steps:

suspending a compound of formula I in an inert solvent to obtain the crystal form A through stirring and filtration.

In another preferred embodiment, the inert solvent is selected from isopropyl alcohol or hexane.

In another preferred embodiment, a weight-to-volume ratio of the compound of formula I in the inert solvent is 10-100 mg/mL, preferably 15-50 mg/mL, and more preferably 20-40 mg/mL.

In another preferred embodiment, the stirring has one or more characteristics selected from the group consisting of:

(1) the stirring time being 12-48 hours, and preferably 18-36 hours; and
(2) the stirring temperature being 25±5° C.

The present invention further provides a use of the crystal form A as described in any one of the foregoing or the crystalline composition as previously described, where the crystal form A or the crystalline composition may be used for preparing drugs for preventing and/or treating benign prostate hyperplasia diseases.

The present invention further provides a drug including the crystal form A as described in any one of the foregoing or the crystalline composition as previously described and a pharmaceutically acceptable carrier.

In another preferred embodiment, the carrier is selected from the group consisting of: a filler, a disintegrating agent, a lubricant, or a combination thereof.

In another preferred embodiment, the filler is selected from the group consisting of: pregelatinized starch, lactose, microcrystalline cellulose, dextrin, mannitol, magnesium oxide, calcium sulfate, or a combination thereof.

In another preferred embodiment, the disintegrating agent is selected from the group consisting of: carboxymethyl cellulose and a salt thereof, cross-linked carboxymethyl cellulose and a salt thereof, polyvinylpyrrolidone cross-linked, sodium carboxymethyl starch, low-substituted hydroxypropyl cellulose, or a combination thereof.

In another preferred embodiment, the lubricant is selected from the group consisting of: magnesium stearate, calcium stearate, or a combination thereof.

It should be understood that within the scope of the present invention, the foregoing technical features and the technical features detailed hereunder (such as embodiments) can be combined with each other to constitute a new or preferred technical solution. Due to space limitations, this will be not repeatedly detailed herein.

DETAILED DESCRIPTION OF THE INVENTION

After making the extensive and in-depth study and performing extensive screening and test, the inventors provide a crystal form A of a compound of formula I, where the crystal form A of the compound of the present invention does not contain water and a solvent, has high stability, low hygroscopicity, and ease of processing, and is suitable for patent medicine. The present invention is implemented on this basis.

Terms

Unless otherwise defined, all technical terms and scientific terms used herein have the same meanings as commonly understood by persons of ordinary skills in the art to which the present invention pertains.

As used herein, when used in reference to a specific enumerated value, the term "approximately" means that the value may vary by no more than 1% from the enumerated value. For example, as used herein, the expression "approximately 100" includes all values between 99 and 101 (for example, 99.1, 99.2, 99.3, and 99.4).

As used herein, the terms "contain" or "include" may be inclusive, semi-exclusive, or exclusive. In other words, the terms also include "substantially consisting of" or "consisting of".

As described herein, the terms "compound of formula I" and "S-(−)-2,3-methylenedioxy-5,8,13,13a-tetrahydro-10, 11-dimethoxy-6H-dibenzo[a, g]quinolizine" can be used interchangeably.

As used herein, the term "a quantity of n or more" refers to any positive integer (for example, n, n+1, . . . ) including n and greater than n, where an upper limit Nup is the number of all values in the group. For example, "one or more" includes not only all positive integers of the upper limit Nup of 1, 2, 3, 4, 5, 6, 7, 8, 9, 10, 11, 12, 13, 14, 15, 16, 17, 18, 19, 20, 21, . . . , but also includes "2 or more", "3 or more", "4 or more", 5 or more", "6 or more", "7 or more", "8 or more", "9 or more", "10 or more", "11 or more", "12 or more", "13 or more", "14 or more", "15 or more", or other ranges. For example, "three or more" includes not only all positive integers of the upper limit Nup of 3, 4, 5, 6, 7, 8, 9, 10, 11, 12, 13, 14, 15, 16, 17, 18, 19, 20, 21, . . . , but also includes "4 or more", 5 or more", "6 or more", "7 or more", "8 or more", "9 or more", "10 or more", "11 or more", "12 or more", "13 or more", "14 or more", "15 or more", or other ranges.

As used herein, the term "inert solvent" refers to a solvent that does not react with the compound of formula I of the present invention. Preferably, none of the solvents used in the preparation method for the crystal form A of the present invention reacts with the compound of formula I.

Unless otherwise specified, the term "ambient temperature" or "normal temperature" means that the temperature is 4-32° C., and preferably 25±5° C.

Polymorph

Solid exists either in an amorphous form or in a crystalline form. In the case of crystalline form, molecules are positioned in a three-dimensional crystal lattice. When crystallized from a solution or a slurry, a compound can be crystallized in different spatial lattice arrangements (such property is called "heteromorphism") to form crystals with different crystal forms, where such crystal forms are called "polymorph". Different polymorphs of a given substance may differ from each other in one or more physical properties, such as solubility, dissolution rate, true specific gravity, crystal form, stacking mode, fluidity, and/or solid stability.

As used herein, "crystal form A", "crystal form A of compound of formula I", "crystal form A of the present invention", "crystal form A of S-(−)-2,3-methylenedioxy-5, 8,13,13a-tetrahydro-10,11-dimethoxy-6H-dibenzo[a, g]quinolizine" can be used interchangeably.

Crystal Form A

The present invention provides a crystal form A of a compound of formula I,

I an X-ray powder diffraction pattern of the crystal form A includes three or more 2θ values selected from the group consisting of:
12.21±0.2°, 13.381±0.2°, 15.181±0.2°, 16.171±0.2°, 17.101±0.2°, 19.801±0.2°, 21.511±0.2°, 24.391±0.2°, and 25.321±0.2°.

Further, the X-ray powder diffraction pattern of the crystal form A includes three or more 2θ values selected from the group consisting of:
12.21±0.1°, 13.381±0.1°, 15.181±0.1°, 16.171±0.1°, 17.101±0.1°, 19.801±0.1°, 21.511±0.1°, 24.391±0.1°, and 25.321±0.1°.

Further, a relative intensity corresponding to a position peak of the 2θ value is:

| Angle 2θ | Relative intensity |
|---|---|
| 12.21 ± 0.2° | 100 |
| 13.381 ± 0.2° | 2.5 ± 0.5 |
| 15.181 ± 0.2° | 4.48 ± 0.5 |
| 16.171 ± 0.2° | 7.05 ± 0.5 |
| 17.101 ± 0.2° | 17.79 ± 0.5 |
| 19.801 ± 0.2° | 14.02 ± 0.5 |
| 21.511 ± 0.2° | 6.47 ± 0.5 |
| 24.391 ± 0.2° | 6.56 ± 0.5 |
| 25.321 ± 0.2° | 5.44 ± 0.5 |

Further, the crystal form A has a characteristic peak at d values of three or more interplanar crystal spacings selected from the group consisting of: 7.2 Å±0.2 Å, 6.6 Å±0.2 Å, 5.8 Å±0.2 Å, 5.5 Å±0.2 Å, 5.2 Å±0.2 Å, 4.5 Å±0.2 Å, 4.1 Å±0.2 Å, 3.6 Å±0.2 Å, and 3.5 Å±0.2 Å.

Further, the crystal form A has the XRPD pattern substantially as shown in FIG. 2, or the X-ray powder diffraction pattern of the crystal form A is substantially as shown in Table 1. The 2θ value of each characteristic peak at the 2θ value optionally has an error margin of ±0.2°, or preferably has an error margin of ±0.1°.

Further, the crystal form A has one or more characteristics selected from the group consisting of:
1) a TGA pattern of the crystal form A having no gravimetric loss before the compound of formula I is decomposed;
2) a DSC pattern of the crystal form A having a characteristic absorption peak at a peak of 172±5° C. (or ±3° C., or ±1° C.); and
3) the crystal form A having a moisture-absorption weight gain of no more than 1% and preferably 0.4%±0.3% at a relative humidity of 0%-95%.

In another preferred embodiment, the IR spectrogram of the crystal form A includes three or more characteristic absorption peaks denoted as a wavelength of λ and selected from the group of consisting of: 3599±2 cm$^{-1}$, 3001±2 cm$^{-1}$, 2934±2 cm$^{-1}$, 2835±2 cm$^{-1}$, 2789±2 cm$^{-1}$, 1611±2 cm$^{-1}$, 1520±2 cm$^{-1}$, 1485±2 cm$^{-1}$, 1452±2 cm$^{-1}$, 1348±2 cm$^{-1}$, 1248±2 cm$^{-1}$, 1217±2 cm$^{-1}$, 1107±2 cm$^{-1}$, 1030±2 cm$^{-1}$, 995±2 cm$^{-1}$, 926±2 cm$^{-1}$, and 856±2 cm$^{-1}$; more preferably, each of the characteristic absorption peaks has an error margin of ±1 cm$^{-1}$.

Further, the crystal form A has one or more characteristics selected from the group consisting of:
1) the crystal form A having a TGA pattern substantially as shown in FIG. 3;
2) the crystal form A having a DSC pattern substantially as shown in FIG. 4;
3) the crystal form A having a DVS pattern substantially as shown in FIG. 5; and 4) the crystal form A having an IR spectrogram substantially as shown in FIG. 6.

Crystalline Composition

The present invention further provides a crystalline composition, where the crystalline composition includes the crystal form A according to a first aspect of the present invention.

In another preferred embodiment, based on a total weight of the crystalline composition, a weight percentage of the crystal form A is 60%-99.999%, preferably 80%-99.999%, and more preferably 90%-99.999%.

In another preferred embodiment, the crystalline composition further includes: a crystal of a compound of an amorphous form A in formula I or an amorphous compound of formula I.

Crystallization

Through solution dissolution, the solubility limit of a target compound can be exceeded, thus implementing the crystallization of the compound on a production scale. This can be implemented by various methods, for example, dissolving the compound at a relatively high temperature, and then cooling the solution below a saturation limit thereof. Alternatively, this can also be implemented through boiling, atmospheric evaporation, vacuum drying or some other methods to reduce a liquid volume. The solubility of the compound of interest can be reduced by adding an anti-solvent, a solvent in which the compound has low solubility, or a mixture of such solvents. Another alternative is to adjust a pH value to reduce the solubility of the compound.

If formation and crystallization of salt are expected to occur concurrently and the salt in a reaction medium has less solubility than raw materials, adding an appropriate amount of salt or acid can lead to direct crystallization of the desired salt. Similarly, in a medium whose final desired solubility is less than the solubility of a reactant, the completion of synthesis reaction can cause direct crystallization of a final product.

Optimization of crystallization may include seeding crystals in a desired form into a crystallization medium. In addition, a combination of the above strategies serves as many crystallization methods. In an example, the compound of interest is dissolved in a solvent at a high temperature, and then an appropriate volume of anti-solvent is added in a controlled manner, so that the resulting solution is just below a saturation level. In this case, seeds in a desired form can be added and kept for the integrity thereof, and the resulting solution can be cooled to implement crystallization.

Preparation Method for Crystal Form A

The present invention further provides a preparation method for the crystal form A, and the method includes the following steps:

suspending a compound of formula I in an inert solvent to obtain the crystal form A through stirring and filtration.

In another preferred embodiment, the inert solvent is selected from isopropyl alcohol or hexane.

In another preferred embodiment, a weight-to-volume ratio of the compound of formula I in the inert solvent is 10-100 mg/mL, preferably 15-50 mg/mL, and more preferably 20-40 mg/mL.

In another preferred embodiment, the stirring has one or more characteristics selected from the group consisting of:
  (1) the stirring time being 12-48 hours, and preferably 18-36 hours; and
  (2) the stirring temperature being 25±5° C.

Preferably, raw materials for the foregoing preparation methods are amorphous compounds of formula I.

Typically, crystal forms A obtained by the foregoing preparation methods can be subjected to filtration, drying, and other steps by conventional methods in the art as required.

Preferably, the filtration can be selected from, but not limited to, filtration after centrifugation, pressure filtration, or vacuum filtration. The drying can be selected from, but not limited to, vacuum drying or oven drying.

Pharmaceutical Composition and Use Thereof

The pharmaceutical composition of the present invention includes the crystal form A of a safe and effective amount of the compound of formula I and a pharmaceutically acceptable carrier.

The "active component" of the present invention refers to the compound of formula I described herein, and preferably refers to the crystal form A of the present invention.

Typically, based on a total weight of the active component, a weight percentage of the crystal form A is 60%-99.999%, preferably 80%-99.999%, and more preferably 90%-99.999%.

The crystal form A, crystalline composition, and pharmaceutical composition of the present invention can be used for preventing and/or treating benign prostate hyperplasia diseases.

The "safe and effective amount" means that an amount of compound is enough to obviously alleviate patient's conditions without causing serious side effects. Generally, the pharmaceutical composition includes 1-2000 mg of the crystal form A of the present invention per dose, and more preferably, 10-500 mg of the compound of the present invention per dose. Preferably, the "one dose" is a capsule or a tablet.

The "pharmaceutically acceptable carrier" refers to one or more compatible solid or liquid fillers or gelatinous masses that are suitable for human use and must have sufficient purity and low toxicity. The "compatible" herein means that all components in the composition can be blended with each other or the compound of the present invention, which does not significantly reduce the efficacy of the compound. In some examples, the pharmaceutically acceptable carrier includes cellulose and derivatives thereof (such as sodium carboxymethyl cellulose, sodium carboxyethyl cellulose, and cellulose acetate), gelatin, talc, solid lubricant (such as stearic acid and magnesium stearate), calcium sulfate, vegetable oil (such as soybean oil, sesame oil, peanut oil, and olive oil), polyhydric alcohols (such as propylene glycol, glycerol, mannitol, and sorbitol), emulsifier (such as Tween®), moistening agent (such as sodium dodecyl sulfate), coloring agent, flavoring agent, stabilizer, antioxidant, preservative, reagent water, and the like.

An administration manner of the compound or pharmaceutical composition of the present invention is not particularly limited, and a representative administration manner thereof includes, but is not limited to, oral administration, rectal administration, parenteral administration (intravenous administration, intramuscular administration, or subcutaneous administration), and topical administration.

Generally, a therapeutically effective dose of the crystal form A of the present invention ranges from: approximately 1-2000 mg/day, approximately 10-1000 mg/day, approximately 10-500 mg/day, approximately 10-250 mg/day, approximately 10-100 mg/day, or approximately 10-50 mg/day. The therapeutically effective dose will be administered in one or more doses. However, it should be understood that a specific dose of the compound of the present invention for any specific patient is determined depending on many factors, for example, age, gender, weight, general health, diet, individual response, and administration time of patient to be treated, severity of disease to be treated, as well as activity, dosage form, application mode, and concomitant drug of specific compound to be administered. The therapeutically effective dose in a given situation can be determined by clinicians or doctors through conventional experiments. In any case, the compound or composition will be administered in multiple doses based on the individual conditions of the patient and in a manner that allows the delivery of a therapeutically effective dose.

The present invention has the following main advantages:
(1) The crystal form A of the compound of formula I of the present invention does not contain water and a solvent, has high stability and low hygroscopicity, and is suitable for patent medicine.
(2) The crystal form A of the compound of formula I of the present invention is easy to collect and unlikely to raise and cause waste during the manufacturing of drugs such as sub-packaging, and is helpful to protect the health of operators.
(3) The preparation method for the crystal form A of the compound of formula I of the present invention is simple and convenient, and is suitable for large-scale industrial production.

The following further describes the present invention with reference to specific embodiments. It should be understood that these examples are merely intended to illustrate the present invention but not to limit the scope of the present invention. In the following examples, experimental methods without specific conditions are usually based on conventional conditions or conditions recommended by manufacturers. Unless otherwise specified, percentages and parts are calculated by weight.

Test Method

X-ray diffraction (XRD for short) is a structural analysis method to analyze the spatial distribution of internal atoms in a substance with X-ray diffraction formed by crystals. When irradiated on a crystalline substance, X-rays with a specific wavelength are scattered because they encounter regularly arranged atoms or ions in the crystals, and phases of the scattered X-rays are strengthened in some directions, which shows a specific diffraction phenomenon corresponding to a crystalline texture.

In the present invention, test parameters of the XRD are as follows: device model: Bruker D8advance; target: Cu-Kα (40 kV, 40 mA); distance from a sample to a detector: 30 cm; scanning range: 3°-40° (2θ value); and scanning step size: 0.1s.

Thermo gravimetric analysis (TGA for short) is an analysis technique to determine the change of mass of substances with temperature under conditions of programmed temperature control. Heat generated by the thermo change of the sample can be obtained through thermo gravimetric analysis. Thus, such thermo gravimetric analysis is suitable for detecting the loss of crystallization solvents or crystallization water molecules in crystalline substances or the process and magnitude of sublimation and decomposition of the sample, and can also effectively distinguish whether the substances contain the crystallization solvents or the crystallization water molecules.

In the present invention, test parameters of the TGA are as follows: device model: Netzsch TG 209F3; temperature range: 30-400° C.; scanning rate: 10 k/min; purge gas: 25 ml/min; and protective gas: 15 mL/min.

Differential scanning calorimetry (DSC for short) is a technique to determine a heat difference between a sample and an inert reference compound ($\alpha$-$Al_2O_3$ commonly used) with the change of temperature through programmed temperature rise or cooling control. DSC detection is suitable for analyzing the state of sample decomposition by fusion, the state of mixed crystal substances, and the state of crystal transformation substances.

In the present invention, test parameters of the DSC are as follows: device model: Perkin Elmer DSC 8500; nitrogen flow rate: 20 mL/min; temperature range: 50-200° C.; and scanning rate: 10° C./min.

Infrared spectrometry (IR for short) is an earliest analysis method used to identify crystalline substances. Because covalent bonds of different crystal molecules have a different electrical environment, the intensity of the covalent bonds may also change, and such change will inevitably lead to different IR spectra of different crystal forms.

In the present invention, test parameters of the IR are as follows: device model: Nicolet 6700 Fourier transform infrared spectrometer; and single-point ATR method with resolution of 4.0 cm$^{-1}$.

Dynamic vapor sorption (DVS) test/hygroscopicity test is to quickly determine the increase and loss of sample moisture caused by a flowing carrier gas with a set relative humidity (RH). The sample is placed on a high-sensitivity and high-stability digital micro-balancer in a self-suspension state, and then the sorption/desorption of water vapor is detected by determining the increase/decrease of material mass, so as to determine the hygroscopicity of the sample.

In the present invention, test parameters of the DVS are as follows: device model: SMS DVS Intrinsic; 0-95% RH; temperature: 25° C.

Polarizing Microscope

In the present invention, the model of the polarizing microscope is XPV-400E.

Example 1

Preparation of crystal form A of S-(−)-2,3-methylenedioxy-5,8,13,13a-tetrahydro-10,11-dimethoxy-6H-dibenzo[a, g]quinolizine crystal 15 mg of S-(−)-2,3-methylenedioxy-5,8,13,13a-tetrahydro-10,11-dimethoxy-6H-dibenzo[a, g]quinolizine was dissolved into 1 ml of isopropyl alcohol, and the mixture was stirred at ambient temperature at 25° C. and equilibrated for at least 24 hours. A solid material obtained through filtration was placed in a vacuum drying oven to obtain a crystal form A of S-(−)-2,3-methylenedioxy-5,8,13,13a-tetrahydro-10,11-dimethoxy-6H-dibenzo[a, g]quinolizine crystal through vacuum drying.

The crystal form A of the crystal prepared in Example 1 was tested for polarizing microscope imaging, XRPD, TGA, DSC, DVS, IR, Raman, and the like, with characterization results shown in FIG. 1-FIG. 7.

Figure 1:
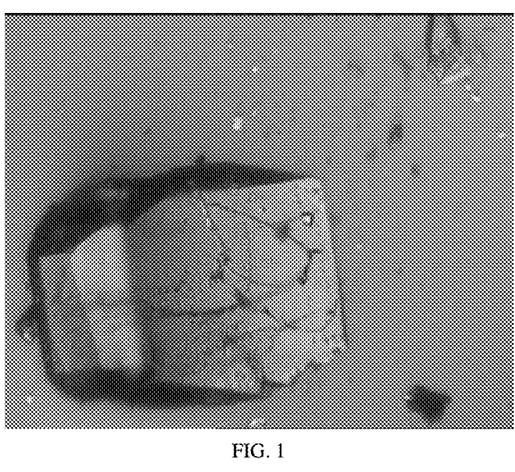
FIG. 1 shows a polarizing microscope photograph of a crystal form A in Example 1.

FIG. 1 shows a polarizing microscope photograph of a crystal form A, and it can be seen from FIG. 1 that the crystal form A is a block-shaped crystal.

FIG. 2 shows an XRPD pattern of a crystal form A (a peak table is as shown in Table 1).

TABLE 1

X-ray powder diffraction peaks of crystal form A

| Angle 2θ | Interplanar crystal spacing | Intensity | Relative intensity |
|---|---|---|---|
| 12.21 | 7.24273 | 881 | 100 |
| 13.381 | 6.61191 | 37 | 2.5 |
| 15.181 | 5.8317 | 44.3 | 4.48 |
| 16.171 | 5.47682 | 81.3 | 7.05 |

TABLE 1-continued

X-ray powder diffraction peaks of crystal form A

| Angle 2θ | Interplanar crystal spacing | Intensity | Relative intensity |
|---|---|---|---|
| 17.101 | 5.18099 | 75.4 | 17.79 |
| 19.801 | 4.48017 | 103 | 14.02 |
| 21.511 | 4.12771 | 53.2 | 6.47 |
| 24.391 | 3.64643 | 48.8 | 6.56 |
| 25.321 | 3.51457 | 37 | 5.44 |

FIG. 3 shows a TGA pattern of a crystal form A. It can be seen from FIG. 3 that the crystal form A has no gravimetric loss before the compound is decomposed, indicating that the crystal form A does not contain water or other solvents.

FIG. 4 shows a differential scanning calorimetry (DSC) pattern of a crystal form A. It can be seen from FIG. 4 that DSC corresponding to the crystal form A shows that a fusion peak temperature is 172.5° C. at oneset of approximately 170.3° C.

FIG. 5 shows a dynamic vapor sorption (DVS) pattern of a crystal form A. It can be seen from FIG. 5 that the crystal form A has slight change in hygroscopicity (approximately 0.6%) and weight at relative humidity of 0-95%, indicating that the crystal form A has low hygroscopicity.

FIG. 6 shows an infrared (IR) spectrogram of a crystal form A. It can be seen from FIG. 6 that the crystal form A has characteristic absorption peaks at 3599±2 cm$^{-1}$, 3001±2 cm$^{-1}$, 2934±2 cm$^{-1}$, 2835±2 cm$^{-1}$, 2789±2 cm$^{-1}$, 1611±2 cm$^{-1}$, 1520±2 cm$^{-1}$, 1485±2 cm$^{-1}$, 1452±2 cm$^{-1}$, 1348±2 cm$^{-1}$, 1248±2 cm$^{-1}$, 1217±2 cm$^{-1}$, 1107±2 cm$^{-1}$, 1030±2 cm$^{-1}$, 995±2 cm$^{-1}$, 926±2 cm$^{-1}$, and 856±2 cm$^{-1}$.

Example 2

Preparation of crystal form A of S-(−)-2,3-methylenedioxy-5,8,13,13a-tetrahydro-10,11-dimethoxy-6H-dibenzo[a, g]quinolizine crystal 215 mg of S-(−)-2,3-methylenedioxy-5,8,13,13a-tetrahydro-10,11-dimethoxy-6H-dibenzo[a, g]quinolizine was dissolved into 1 ml of hexane, and the mixture was stirred at ambient temperature at 25° C. and equilibrated for at least 24 hours. A solid material obtained through filtration was placed in a vacuum drying oven to obtain a crystal form A of S-(−)-2,3-methylenedioxy-5,8,13,13a-tetrahydro-10,11-dimethoxy-6H-dibenzo[a, g]quinolizine crystal through vacuum drying.

An obtained product has substantially same XRPD results as Example 1.

Comparative Example 1

Preparation of crystal form B of S-(−)-2,3-methylenedioxy-5,8,13,13a-tetrahydro-10,11-dimethoxy-6H-dibenzo[a, g]quinolizine crystal 15 mg of S-(−)-2,3-methylenedioxy-5,8,13,13a-tetrahydro-10,11-dimethoxy-6H-dibenzo[a, g]quinolizine was dissolved into 1 ml of methanol, and the mixture was stirred at ambient temperature at 25° C. and equilibrated for at least 24 hours. A solid material obtained through filtration was placed in a vacuum drying oven to obtain a crystal form B through vacuum drying.

An obtained product has substantially same XRPD results as Example 7.

Comparative Example 2

Preparation of crystal form C of S-(−)-2,3-methylenedioxy-5,8,13,13a-tetrahydro-10,11-dimethoxy-6H-dibenzo[a, g]quinolizine crystal Approximately 3 mg of S-(−)-2,3-methylenedioxy-5,8,13,13a-tetrahydro-10,11-dimethoxy-6H-dibenzo[a, g]quinolizine was dissolved into 200 μl of ethyl alcohol and 100 μl of isopropyl alcohol, followed by being mixed well and dissolved; and the mixture was slowly volatilized to be dry at 25° C. to obtain the crystal form C.

An obtained product has substantially same XRPD results as Example 8.

Comparative Example 3

Preparation of crystal form D of S-(−)-2,3-methylenedioxy-5,8,13,13a-tetrahydro-10,11-dimethoxy-6H-dibenzo[a, g]quinolizine crystal Approximately 3 mg of S-(−)-2,3-methylenedioxy-5,8,13,13a-tetrahydro-10,11-dimethoxy-6H-dibenzo[a, g]quinolizine was dissolved into 200 μl of isopropyl alcohol and 600 μl of chloroform, followed by being mixed well and dissolved; and the mixture was slowly volatilized at 25° C. to obtain the crystal form D.

An obtained product has substantially same XRPD results as Example 9.

Transformation Experiment Between Crystal Forms

Four crystal forms, such as Form A, Form B, Form C, and Form D, are experienced for mutual transformation experiment. Experimental conditions and results are as follows:

TABLE 2

Comparison of crystal form stability

| Initial sample | Heating temperature (° C.) | Heating time (min) | Crystal form of product |
|---|---|---|---|
| Form A | 120 | 40 | Form A |
| Form B | 120 | 40 | Form A |
| Form C | 120 | 40 | Form A |
| Form D | 120 | 40 | Form A |

5 mg of each sample is taken and mixed with 1 ml of a solvent at 25° C. Experimental conditions and results are as follows:

TABLE 3

Comparison of crystal form stability (equilibrated suspension)

| Mixture of initial sample | Composition of suspension solvent | Suspension time (day) | Crystal form of product |
|---|---|---|---|
| Form A + Form B | Isopropyl alcohol | 2 | Form A |
| Form A + Form C | Isopropyl alcohol | 2 | Form A |
| Form A + Form D | Isopropyl alcohol | 2 | Form A |
| Form B + Form C | Isopropyl alcohol | 2 | Form A |
| Form B + Form D | Isopropyl alcohol | 2 | Form A |
| Form C + Form D | Isopropyl alcohol | 2 | Form A |

It can be seen from the crystal transformation results that Form A is a most stable crystal form.

Investigation of Hygroscopicity

A dynamic vapor sorption (DVS) device is used to investigate the moisture sorption and desorption of samples at a temperature of 25° C. and a relative humidity of 0-95%, so as to determine the hygroscopic sorption properties of different crystal forms. Experimental results are as follows:

TABLE 4

Comparison of hygroscopicity of crystal form

| Crystal form | Percentage of solvent or water (%) | Hygroscopicity |
|---|---|---|
| Form A | 0.0 | RH (65%), water absorption percentage (0.1%) |
|  |  | RH (80%), water absorption percentage (0.2%) |
| Form B | 10.8 | RH (65%), water loss percentage (0.2%) |
|  |  | RH (80%), water loss percentage (0.3%) |
| Form C | 4.4 | RH (65%), water absorption percentage (0.5%) |
|  |  | RH (80%), water absorption percentage (1.2%) |
| Form D | 0.0 | RH (65%), water absorption percentage (0.2%) |
|  |  | RH (80%), water absorption percentage (0.3%) |

Study on Preparation and Stability of Drug Composition
1. Prescription of Pharmaceutical Composition:

| Component | Dose |
|---|---|
| Active pharmaceutical ingredient (crystal form A/B/C/D) | 1 part |
| Sucrase | 24 parts |
| Lactose | 24 parts |
| Polyvinylpyrrolidone cross-linked (CL-M) | 0.3 parts |
| Povidone K30 | 0.3 parts |

2. Preparation process:
① Povidone K30 is weighed according to prescription and dissolved into 80% ethanol, to prepare an adhesive.
② Active pharmaceutical ingredients (crystal form A/B/C/D) and auxiliary ingredients such as sucrose/lactose/polyvinylpyrrolidone cross-linked (CL-M) are mixed well, and the mixture is added with the adhesive, to prepare a soft material.
③ Granulation is performed by a 20-mesh sieve.
④ Drying is performed at 50° C., and moisture is controlled to be less than 2.0%.
⑤ The 20-mesh sieve is used for straightening granulates, and a 80-mesh sieve is used for removing fine powder.
⑥ The granulates are collected.
⑦ Inner package is adopted for the collected granulates.
3. Stability study data:
Four batches of pilot-scale samples prepared according to the preparation process, including sample A, sample B, sample C, and sample D, respectively. According to the guiding principle of stability test of active pharmaceutical ingredients and pharmaceutic preparations in Appendix XIXC of China Pharmacopoeia (2015 II), an accelerated stability test is carried out for the four batches of samples.
Conditions for the accelerated stability test: the above samples are respectively packaged by polyester/aluminum/polyethylene composite membranes for packaging, placed for 6 months at a temperature of 40° C. and a relative humidity of 75%. During the test, samples are taken once at 0, 1, 3, and 6 months respectively, and inspected according to stability test items thereof.

TABLE 5

Investigation results of accelerated test

| | | Related substances (%) | | | |
|---|---|---|---|---|---|
| | Test item | Sample A | Sample B | Sample C | Sample D |
| 0 months | Maximum single impurity | Not detected | 0.08 | 0.09 | 0.08 |
| | Total impurity | Not detected | 0.31 | 0.34 | 0.31 |
| | Dissolution rate | 100.1 | 91.4 | 90.6 | 92.3 |
| 1 month | Maximum single impurity | 0.06 | 0.23 | 0.25 | 0.24 |
| | Total impurity | 0.06 | 0.47 | 0.53 | 0.48 |
| | Dissolution rate | 98.5 | 89.7 | 89.4 | 91.2 |
| 2 months | Maximum single impurity | 0.15 | 0.34 | 0.36 | 0.33 |
| | Total impurity | 0.15 | 0.57 | 0.64 | 0.61 |
| | Dissolution rate | 103.5 | 89.6 | 89.1 | 90.4 |
| 3 months | Maximum single impurity | 0.20 | 0.47 | 0.53 | 0.52 |
| | Total impurity | 0.20 | 0.78 | 0.87 | 0.83 |
| | Dissolution rate | 97.2 | 89.1 | 88.9 | 90.3 |
| 6 months | Maximum single impurity | 0.20 | 0.82 | 0.97 | 0.95 |
| | Total impurity | 0.25 | 1.36 | 1.43 | 1.41 |
| | Dissolution rate | 98.5 | 88.6 | 88.2 | 89.5 |

It can be seen from the above results that the stability and dissolution of the granules made of crystal form A are better than those of the granules made of other crystal forms, and related substances in the granules of crystal form A have change far less than those of other crystal forms.

It can be seen that the crystal form A of the present invention does not contain water or a solvent, is of a columnar crystal, and has good physical stability and relatively low hygroscopicity at a relative humidity of 0-95%. Therefore, the crystal form A is very suitable for processing of patent medicine. In addition, the crystal form A of the compound of formula I of the present invention is easy to collect and not easy to raise and cause waste during the manufacturing of drugs such as sub-packaging, and is helpful to protect the health of operators.

All literatures mentioned in the present invention are incorporated by reference herein as if each literature is separately incorporated by reference. In addition, it should be understood that after reading the above lecturing contents of the present invention, persons skilled in the art can make various alterations or modifications to the present invention, and these equivalent forms also fall within the scope defined by claims appended in this application.

What is claimed is:

1. A crystal form A of a compound of formula I, wherein an X-ray powder diffraction pattern of the crystal form A comprises three or more 2θ values selected from the group consisting of:
12.21±0.2°, 13.381±0.2°, 15.181±0.2°, 16.171±0.2°, 17.101±0.2°, 19.801±0.2°, 21.511±0.2°, 24.391±0.2°, and 25.321±0.2°.

2. The crystal form A according to claim 1, wherein the X-ray powder diffraction pattern of the crystal form A comprises the 2θ value selected from the group consisting of:
12.21±0.2°, 13.381±0.2°, 15.181±0.2°, 16.171±0.2°, 17.101±0.2°, 19.801±0.2°, 21.511±0.2°, 24.391±0.2°, and 25.321±0.2°.

3. The crystal form A according to claim 1, wherein a relative intensity corresponding to a position peak of the 2θ value is:

| Angle 2θ | Relative intensity |
|---|---|
| 12.21 ± 0.2° | 100 |
| 13.381 ± 0.2° | 2.5 ± 0.5 |
| 15.181 ± 0.2° | 4.48 ± 0.5 |
| 16.171 ± 0.2° | 7.05 ± 0.5 |
| 17.101 ± 0.2° | 17.79 ± 0.5 |
| 19.801 ± 0.2° | 14.02 ± 0.5 |
| 21.511 ± 0.2° | 6.47 ± 0.5 |
| 24.391 ± 0.2° | 6.56 ± 0.5 |
| 25.321 ± 0.2° | 5.44 ± 0.5. |

4. The crystal form A according to claim 1, wherein the crystal form A has a characteristic peak at three or more d values of interplanar crystal spacings selected from the group consisting of: 7.2 Å±0.2 Å, 6.6 Å±0.2 Å, 5.8 Å±0.2 Å, 5.5 Å±0.2 Å, 5.2 Å±0.2 Å, 4.5 Å±0.2 Å, 4.1 Å±0.2 Å, 3.6 Å±0.2 Å, and 3.5 Å±0.2 Å.

5. The crystal form A according to claim 1, wherein the crystal form A has the XRPD pattern substantially as shown in FIG. 2.

6. The crystal form A according to claim 1, wherein the crystal form A has one or more characteristics selected from the group consisting of:
1) a TGA pattern of the crystal form A having no gravimetric loss before the compound of formula I is decomposed;
2) a DSC pattern of the crystal form A having a characteristic absorption peak at a peak of 172±5; and
3) the crystal form A having a moisture-absorption weight gain of no more than 1% and preferably 0.4%±0.3% at a relative humidity of 0%-95%.

7. The crystal form A according to claim 1, wherein the crystal form A has one or more characteristics selected from the group consisting of:
1) the crystal form A having a TGA pattern substantially as shown in FIG. 3;
2) the crystal form A having a DSC pattern substantially as shown in FIG. 4;
3) the crystal form A having a DVS pattern substantially as shown in FIG. 5; and
4) the crystal form A having an IR spectrogram substantially as shown in FIG. 6.

8. A crystalline composition, comprising the crystal form A according to claim 1.

9. A preparation method for the crystal form A according to claim 1, wherein the method comprises:
suspending a compound of formula I in an inert solvent to obtain the crystal form A through stirring and filtration, wherein the inert solvent is selected from isopropyl alcohol or hexane.

* * * * *